(12) United States Patent
Chaki et al.

(10) Patent No.: US 9,938,209 B2
(45) Date of Patent: Apr. 10, 2018

(54) METHOD FOR PRODUCING 2,3,3,3-TETRAFLUOROPROPENE

(71) Applicant: DAIKIN INDUSTRIES, LTD., Osaka (JP)

(72) Inventors: Takehiro Chaki, Osaka (JP); Kazuhiro Takahashi, Osaka (JP); Tatsuya Takakuwa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/190,567

(22) Filed: Jun. 23, 2016

(65) Prior Publication Data

US 2016/0304419 A1    Oct. 20, 2016

Related U.S. Application Data

(62) Division of application No. 14/903,411, filed as application No. PCT/JP2014/068148 on Jul. 8, 2014.

(30) Foreign Application Priority Data

Jul. 12, 2013  (JP) ................................. 2013-146364

(51) Int. Cl.
*C07C 17/087*  (2006.01)
*C07C 17/20*  (2006.01)
*C07C 17/25*  (2006.01)
*C07C 17/383*  (2006.01)

(52) U.S. Cl.
CPC .......... *C07C 17/087* (2013.01); *C07C 17/202* (2013.01); *C07C 17/206* (2013.01);
(Continued)

(58) Field of Classification Search
CPC ...... C07C 17/25; C07C 17/206; C07C 17/087
See application file for complete search history.

(56) References Cited

U.S. PATENT DOCUMENTS 8,058,486 B2 * 11/2011 Merkel .................. C01B 7/035
570/135
8,158,836 B2    4/2012 Pigamo et al.
(Continued)

FOREIGN PATENT DOCUMENTS

JP    2003-286207    10/2003
JP    2009-227675    10/2009
(Continued)

OTHER PUBLICATIONS

Office Action dated Jul. 7, 2016 in corresponding U.S. Appl. No. 14/903,411.
(Continued)

*Primary Examiner* — Medhanit W Bahta
(74) *Attorney, Agent, or Firm* — Wenderoth, Lind & Ponack, L.L.P.

(57) ABSTRACT

This invention provides a method for producing 2,3,3,3-tetrafluoropropene or 2-chloro-1,1,1,2-tetrafluoropropane, which is a precursor of 2,3,3,3-tetrafluoropropene, in two or three reaction steps, using at least one chlorine-containing compound selected from the group consisting of 1,1,1,2,3-pentachloropropane, 2,3-dichloro-1,1,1-trifluoropropane, and 1,1,2,3-tetrachloropropene as a starting material, the reaction products of at least two of the steps being supplied to the same distillation apparatus to subject the products to a separation operation simultaneously. With this method, 2,3,3,3-tetrafluoropropene or 2-chloro-1,1,1,2-tetrafluoropropane, which is a precursor of 2,3,3,3-tetrafluoropropene, can be efficiently produced with reduced energy and equipment costs in an economically advantageous manner.

6 Claims, 2 Drawing Sheets

(52) U.S. Cl.
CPC ............ *C07C 17/25* (2013.01); *C07C 17/383* (2013.01); *Y02P 20/582* (2015.11)

(56) References Cited

U.S. PATENT DOCUMENTS

| 8,207,384 B2* | 6/2012 | Wendlinger | B01J 23/866 |
| | | | 570/160 |
| 2009/0240090 A1 | 9/2009 | Merkel | |
| 2012/0078020 A1* | 3/2012 | Elsheikh | C07C 17/206 |
| | | | 570/160 |

FOREIGN PATENT DOCUMENTS

| JP | 2012-524026 | 10/2012 |
| WO | 2007/079431 | 7/2007 |
| WO | 2010/123154 | 10/2010 |
| WO | 2011/077394 | 6/2011 |
| WO | 2012/154227 | 11/2012 |
| WO | 2013-088195 | 6/2013 |

OTHER PUBLICATIONS

International Search Report dated Sep. 22, 2014 in corresponding (PCT) Application No. PCT/JP2014/068148.
Decision of Refusal issued May 26, 2015 in corresponding Japanese Application No. 2013-146364, with machine translation.
Extended European Search Report dated Feb. 9, 2017 in corresponding European Application No. 14823042.8.

* cited by examiner

METHOD FOR PRODUCING 2,3,3,3-TETRAFLUOROPROPENE

TECHNICAL FIELD

The present invention relates to a method for producing 2,3,3,3-tetrafluoropropene.

BACKGROUND ART

Fluoroolefins represented by the formula: $CF_3(CX_2)_nCF=CH_2$, the formula: $CF_3(CX_2)_nCH=CHF$, and the like are useful compounds as various functional materials, solvents, refrigerants, blowing agents, and monomers for functional polymers or starting materials of such monomers. For example, fluoroolefins are used as monomers for modifying ethylene-tetrafluoroethylene copolymers. In particular, of the fluoroolefins mentioned above, 2,3,3,3-tetrafluoropropene (HFO-1234yf) represented by $CF_3CF=CH_2$ has recently gained attention because it offers promising prospects as a refrigerant compound of low global-warming potential.

A known method for producing 2,3,3,3-tetrafluoropropene is a method in which halopropane or halopropene used as a starting material is fluorinated with hydrogen fluoride. For example, when 1,1,1,2,3-pentachloropropane (HCC-240db) used as a starting material is fluorinated in a gas phase, the reactions proceed in the route as described below.

$$CCl_3CHClCH_2Cl + 3HF \rightarrow CF_3CCl=CH_2 + 4HCl \quad (1)$$

$$CF_3CCl=CH_2 + HF \rightarrow CF_3CF=CH_2 + HCl \quad (2)$$

In these reactions, the reaction rate in the reaction for producing 2-chloro-3,3,3-trifluoropropene (HCFO-1233xf) from 1,1,1,2,3-pentachloropropane (first reaction) is significantly different from that in the reaction for producing 2,3,3,3-tetrafluoropropene from 2-chloro-3,3,3-trifluoropropene (second reaction). Thus, it is inefficient to perform these reactions using a single reactor, and it is ideal to perform the reactions using separate reactors.

Further, regarding the second reaction, i.e., the step of producing 2,3,3,3-tetrafluoropropene from 2-chloro-3,3,3-trifluoropropene, a method for producing 2,3,3,3-tetrafluoropropene in two reaction steps of adding hydrogen fluoride to 2-chloro-3,3,3-trifluoropropene, and then performing a dehydrochlorination reaction, is known.

For example, Patent Literature 1 listed below discloses a method in which fluorination is performed using halopropane or halopropene as a starting material in a gas phase in three steps under conditions according to each reaction, using three reactors containing different catalysts. Patent Literature 2 listed below discloses an integrated process using these reactions.

Figure 1:
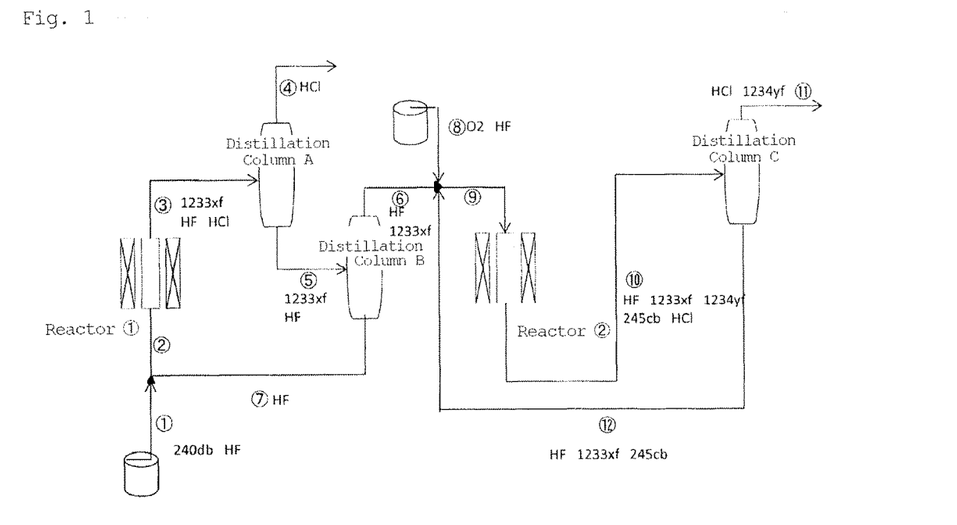
FIG. 1 shows a flow diagram of the general reaction process used in Comparative Example 1 for producing 2,3,3,3-tetrafluoropropene using in 1,1,1,2,3-pentachloropropane as a starting material.

In these methods, however, it is difficult to obtain 100% conversion in the reaction of each step, and it is necessary to separate the unreacted starting materials and the target product from the reaction mixture to recycle the unreacted starting materials. Further, impurities, such as hydrogen chloride, contained in the reaction products tend to cause catalyst deterioration and a decrease in selectivity due to the occurrence of a side reaction in the next step. Thus, after the completion of each step, unwanted substances, such as hydrogen chloride, are generally removed from the reaction mixture using a distillation column, and components used as starting materials of the next step and the unreacted starting materials are separated. Regarding a method for producing 2,3,3,3-tetrafluoropropene using 1,1,1,2,3-pentachloropropane (HCC-240db) as a starting material in the two reaction steps described above, i.e., through the first reaction and the second reaction, FIG. 1 shows a flow diagram of a conventional typical treatment process. As shown in FIG. 1, the conventional method requires the following process: after the high-temperature reaction gases obtained in the first reaction, which contains 2-chloro-3,3,3-trifluoropropene, are cooled and HCl is removed in a purification step, the components are heated again to allow a reaction to proceed at a high temperature in the step of obtaining 2,3,3,3-tetrafluoropropene, and the gases obtained from the outlet of the second reaction step is cooled again to obtain the desired 2,3,3,3-tetrafluoropropene. Further, when unreacted 1,1,1,2,3-pentachloropropane and intermediates, such as 2-chloro-3,3,3-trifluoropropene, are recycled to the corresponding reaction steps, they must be reheated together with HF cooled in each purification step. As described above, the general production process, which requires repeated heating and cooling of the starting material gases, intermediates, products, and the like, results in significant energy loss and an increase in operating costs. The number of distillation columns required for separation is also increased, leading to an increase in equipment costs.

CITATION LIST

Patent Literature

PTL 1: WO2007/079431
PTL 2: JP2009-227675A

SUMMARY OF INVENTION

Technical Problem

The present invention has been accomplished in view of the state of the art described above, and its primary object is to provide a method for producing 2,3,3,3-tetrafluoropropene or 2-chloro-1,1,1,2-tetrafluoropropane (HCFC-244bb), which is a precursor of 2,3,3,3-tetrafluoropropene, in two or three reaction steps, using at least one chlorine-containing compound selected from the group consisting of 1,1,1,2,3-pentachloropropane (HCC-240db), 2,3-dichloro-1,1,1-trifluoropropane (HCFC-243db), and 1,1,2,3-tetrachloropropene (HCO-1230xa) as a starting material, in which the desired product can be efficiently produced with reduced energy and equipment costs in an economically advantageous manner.

Solution to Problem

The present inventors conducted extensive research to achieve the above object, and found the following. Specifically, in the method for producing 2,3,3,3-tetrafluoropropene or its precursor using the above-mentioned specific chlorine-containing compounds as a starting material in two or three reaction steps, when the products of the plurality of reaction steps are simultaneously subjected to distillation treatment using the same distillation apparatus instead of conventional distillation treatment, which is performed using a separate distillation apparatus after the completion of each reaction step, the number of distillation apparatuses can be decreased to thus reduce equipment costs, and energy costs associated with heating and cooling can also be reduced, while sufficiently achieving the object of separating hydrogen chloride, the unreacted starting materials, intermediates, etc. The present inventors further found that performing the reaction steps in parallel is very advantageous in terms of costs because it makes it easy to independently carry out each reaction step under optimum conditions, thus improving conversion and selectivity. The present inventors conducted further extensive research based on these findings, and accomplished the present invention.

More specifically, the present invention provides the following method for producing 2,3,3,3-tetrafluoropropene or 2-chloro-1,1,1,2-tetrafluoropropane, which is a precursor of 2,3,3,3-tetrafluoropropene.

Item 1. A method for producing 2,3,3,3-tetrafluoropropene, comprising the reaction steps of:
(1) obtaining 2-chloro-3,3,3-trifluoropropene by reacting a fluorinating agent with at least one chlorine-containing compound selected from the group consisting of 1,1,1,2,3-pentachloropropane, 2,3-dichloro-1,1,1-trifluoropropane, and 1,1,2,3-tetrachloropropene; and
(2) obtaining 2,3,3,3-tetrafluoropropene by reacting the 2-chloro-3,3,3-trifluoropropene with anhydrous hydrogen fluoride in a gas phase in the presence of a fluorination catalyst while heating,
the method further comprising the step of supplying the products of reaction step (1) and the products of reaction step (2) to the same distillation apparatus to separate the products into a hydrogen chloride-containing fraction and a fraction substantially free of hydrogen chloride.

Item 2. A method for producing 2,3,3,3-tetrafluoropropene, comprising the reaction steps of:
(1) obtaining 2-chloro-3,3,3-trifluoropropene by reacting a fluorinating agent with at least one chlorine-containing compound selected from the group consisting of 1,1,1,2,3-pentachloropropane, 2,3-dichloro-1,1,1-trifluoropropane, and 1,1,2,3-tetrachloropropene;
(2) obtaining 2-chloro-1,1,1,2-tetrafluoropropane by adding hydrogen fluoride to the 2-chloro-3,3,3-trifluoropropene; and
(3) obtaining 2,3,3,3-tetrafluoropropene by dehydrochlorination of the 2-chloro-1,1,1,2-tetrafluoropropane,
the method further comprising the step of supplying the products of two or more of reaction steps (1) to (3) to the same distillation apparatus to separate the products into a hydrogen chloride-containing fraction and a fraction substantially free of hydrogen chloride.

Item 3. The method for producing 2,3,3,3-tetrafluoropropene according to Item 1 or 2, wherein reaction step (1) is performed by reacting anhydrous hydrogen fluoride with at least one chlorine-containing compound selected from the group consisting of 1,1,1,2,3-pentachloropropane, 2,3-dichloro-1,1,1-trifluoropropane, and 1,1,2,3-tetrachloropropene in a gas phase in the presence of a fluorination catalyst while heating.

Item 4. A method for producing 2,3,3,3-tetrafluoropropene, comprising the reaction steps of:
(1) obtaining 2-chloro-1,1,1,2-tetrafluoropropane by adding hydrogen fluoride to 2-chloro-3,3,3-trifluoropropene; and
(2) obtaining 2,3,3,3-tetrafluoropropene by dehydrochlorination of the 2-chloro-1,1,1,2-tetrafluoropropane,
the method further comprising the step of supplying the products of reaction step (1) and the products of reaction step (2) to the same distillation apparatus to separate the products into a hydrogen chloride-containing fraction and a fraction substantially free of hydrogen chloride.

Item 5. The method for producing 2,3,3,3-tetrafluoropropene according to any one of Items 1 to 4, further comprising the step of removing hydrogen chloride from the hydrogen chloride-containing fraction.

Item 6. The method for producing 2,3,3,3-tetrafluoropropene according to Item 5, further comprising the step of recycling all or part of the fraction from which hydrogen chloride has been removed to at least one of the reaction steps.

Item 7. The method for producing 2,3,3,3-tetrafluoropropene according to any one of Items 1 to 6, further comprising the step of collecting 2,3,3,3-tetrafluoropropene from the hydrogen chloride-containing fraction and/or the fraction substantially free of hydrogen chloride.

Item 8. The method for producing 2,3,3,3-tetrafluoropropene according to any one of Items 1 to 7, further comprising the step of recycling all or part of the fraction substantially free of hydrogen chloride to at least one of the reaction steps.

Item 9. A method for producing 2-chloro-1,1,1,2-tetrafluoropropane, comprising the reaction steps of:
(1) obtaining 2-chloro-3,3,3-trifluoropropene by reacting a fluorinating agent with at least one chlorine-containing compound selected from the group consisting of 1,1,1,2,3-pentachloropropane, 2,3-dichloro-1,1,1-trifluoropropane, and 1,1,2,3-tetrachloropropene; and
(2) obtaining 2-chloro-1,1,1,2-tetrafluoropropane by adding hydrogen fluoride to the 2-chloro-3,3,3-trifluoropropene,
the method further comprising the step of supplying the products of reaction step (1) and the products of reaction step (2) to the same distillation apparatus to separate the products into a hydrogen chloride-containing fraction and a fraction substantially free of hydrogen chloride.

Item 10. The method for producing 2-chloro-1,1,1,2-tetrafluoropropane according to Item 9, wherein reaction step (1) is performed by reacting anhydrous hydrogen fluoride with at least one chlorine-containing compound selected from the group consisting of 1,1,1,2,3-pentachloropropane, 2,3-dichloro-1,1,1-trifluoropropane, and 1,1,2,3-tetrachloropropene in a gas phase in the presence of a fluorination catalyst while heating.

Item 11. The method for producing 2-chloro-1,1,1,2-tetrafluoropropane according to Item 9 or 10, further comprising the step of removing hydrogen chloride from the hydrogen chloride-containing fraction.

Item 12. The method for producing 2-chloro-1,1,1,2-tetrafluoropropane according to Item 11, further comprising the step of recycling all or part of the fraction from which hydrogen chloride has been removed to at least one of the reaction steps.

Item 13. The method for producing 2-chloro-1,1,1,2-tetrafluoropropane according to any one of Items 9 to 12, further comprising the step of collecting 2-chloro-1,1,1,2-tetrafluoropropane from the hydrogen chloride-containing fraction and/or the fraction substantially free of hydrogen chloride.

Item 14. The method for producing 2-chloro-1,1,1,2-tetrafluoropropane according to any one of Items 9 to 13, further comprising the step of recycling all or part of the fraction substantially free of hydrogen chloride to at least one of the reaction steps.

The method of the present invention is described in detail below.

(1) Features of the Method of the Present Invention

The method of the present invention produces 2,3,3,3-tetrafluoropropene (HFO-1234yf) or 2-chloro-1,1,1,2-tetrafluoropropane (HCFC-244bb), which is a precursor of 2,3,3,3-tetrafluoropropene, using at least one chlorine-containing compound selected from the group consisting of 1,1,1,2,3-pentachloropropane (HCC-240db), 2,3-dichloro-1, 1,1-trifluoropropane (HCFC-243db), and 1,1,2,3-tetrachloropropene (HCO-1230xa) as a starting material.

First, in the trifluoropropene-producing step of this method, the chlorine-containing compound used as a starting material is reacted with a fluorinating agent to produce 2-chloro-3,3,3-trifluoropropene.

Subsequently, in the tetrafluoropropene-producing procedure, the desired 2,3,3,3-tetrafluoropropene is produced by fluorination of the 2-chloro-3,3,3-trifluoropropene. The tetrafluoropropene-producing procedure can be performed in a single reaction step in which 2-chloro-3,3,3-trifluoropropene is reacted with anhydrous hydrogen fluoride in a gas phase to directly convert the 2-chloro-3,3,3-trifluoropropene into 2,3,3,3-tetrafluoropropene, or in two reaction steps in which hydrogen fluoride is added to 2-chloro-3,3,3-trifluoropropene to obtain 2-chloro-1,1,1,2-tetrafluoropropane and then 2,3,3,3-tetrafluoropropene is obtained by dehydrochlorination of the 2-chloro-1,1,1,2-tetrafluoropropane.

In the method of the present invention, in which 2,3,3,3-tetrafluoropropene or 2-chloro-1,1,1,2-tetrafluoropropane, which is a precursor of 2,3,3,3-tetrafluoropropene, is produced in two or three reaction steps, using the chlorine-containing compound described above as a starting material, the products of at least two of the reaction steps are supplied to the same distillation apparatus to subject the products to a distillation operation simultaneously. This method can reduce the number of distillation apparatuses that are conventionally used individually after each reaction step, and reduce apparatus costs. Further, since the reaction products of at least two of the reaction steps are subjected to a distillation operation simultaneously, the number of cooling and subsequent heating operations in the distillation step individually performed after each reaction step can be reduced, which is advantageous in terms of energy costs. Performing the reaction steps in parallel enables each reaction step to be independently carried out under optimum conditions.

The method of the present invention having these features makes it possible to efficiently obtain 2,3,3,3-tetrafluoropropene or 2-chloro-1,1,1,2-tetrafluoropropane with reduced energy and equipment costs in an economically advantageous manner.

The trifluoropropene-producing step and tetrafluoropropene-producing procedure of the present invention are described in detail below.

(1) Trifluoropropene-Producing Step

In the trifluoropropene-producing step, at least one chlorine-containing compound selected from the group consisting of 1,1,1,2,3-pentachloropropane, 2,3-dichloro-1,1,1-trifluoropropane, and 1,1,2,3-tetrachloropropene is used as a starting material and reacted with a fluorinating agent in the presence or absence of a catalyst to perform a fluorination reaction. Thereby, 2-chloro-3,3,3-trifluoropropene can be obtained.

Examples of usable fluorinating agents include anhydrous hydrogen fluoride, fluorine, trifluoromethane, and the like. In particular, anhydrous hydrogen fluoride is preferred.

1,1,1,2,3-pentachloropropane, 2,3-dichloro-1,1,1-trifluoropropane, and 1,1,2,3-tetrachloropropene used as starting materials are known compounds that can be easily obtained.

A method in which fluorination is performed by conducting a reaction using anhydrous hydrogen fluoride in a gas phase in the presence of a fluorination catalyst is described in detail below as an example of the trifluoropropene-producing step.

Examples of usable fluorination catalysts include known catalysts that are active in a fluorination reaction with hydrogen fluoride. In particular, it is preferable to use a chromium-atom-containing fluorination catalyst. By using such a catalyst and reacting the chlorine-containing compound and anhydrous hydrogen fluoride used as starting materials according to the conditions described below, 2-chloro-3,3,3-trifluoropropene (HCFC-1233xf) can be obtained with high selectivity.

Examples of usable chromium-atom-containing fluorination catalysts include halides, oxides, and the like. Of these, examples of preferred catalysts include $CrCl_2$, $CrF_3$, $Cr_2O_3$, $CrO_2$, $CrO_3$, and the like. These catalysts may be supported on a carrier. There is no particular limitation on the carrier, and examples of carriers include porous alumina silicates typified by zeolite, aluminum oxide, silicon oxide, activated carbon, titanium oxide, zirconium oxide, zinc oxide, aluminum fluoride, and the like.

In the present invention, it is particularly preferable to use at least one catalyst selected from the group consisting of chromium oxide and fluorinated chromium oxide.

Among these catalysts, the chromium oxide, for instance, is not particularly limited. For example, it is preferable to use chromium oxide represented by the composition formula: $CrO_m$, wherein m falls within the range of preferably $1.5<m<3$, more preferably $2<m<2.75$, and even more preferably $2<m<2.3$. Any chromium oxide catalysts in the form of powder, pellets, or the like may be used, as long as they are suitable for the reaction. Of these, chromium oxide catalysts in the form of pellets are preferred. The above chromium oxide catalysts can be prepared, for example, by the method disclosed in JPH05-146680A.

In addition, the fluorinated chromium oxide can be prepared by the method disclosed in JPH05-146680A. For example, it can be prepared by fluorinating the chromium oxide obtained by the above method with hydrogen fluoride (HF treatment).

The degree of fluorination is not particularly limited. For example, fluorinated chromium oxide having a fluorine content of about 10 to about 45% by weight may be suitably used.

Further, a chromium-based catalyst as disclosed in JPH11-171806A may also be used as a chromium oxide catalyst or fluorinated chromium oxide catalyst. The chromium-based catalyst comprises, as a main component, a chromium compound containing at least one metallic element selected from the group consisting of the metallic elements disclosed in JPH11-171806A, i.e., indium, gallium, cobalt, nickel, zinc, and aluminum, and other metallic elements, i.e., vanadium, niobium, and indium. The chromium-based catalyst may be amorphous, partly crystalline, or entirely crystalline.

The anhydrous hydrogen fluoride may be generally supplied to the reactor together with the chlorine-containing compound used as a starting material. The amount of anhydrous hydrogen fluoride is not particularly limited. To achieve high selectivity of 2-chloro-3,3,3-trifluoropropene, the amount of anhydrous hydrogen fluoride is preferably about 3 mol or more, and more preferably about 8 mol or more, per mol of the chlorine-containing compound used as a starting material. When the amount of anhydrous hydrogen fluoride is less than this range, the selectivity of 2-chloro-3,3,3-trifluoropropene and catalytic activity tend to undesirably decrease.

The upper limit of the amount of anhydrous hydrogen fluoride is not particularly limited. An excessively large amount of hydrogen fluoride has little influence on selectivity and conversion. However, productivity decreases because the amount of hydrogen fluoride to be separated increases during purification. For this reason, the amount of anhydrous hydrogen fluoride is generally preferably about 100 mol or less, and more preferably about 50 mol or less, per mol of the chlorine-containing compound used as a starting material.

A method in which a fluorination catalyst is placed into a tubular flow reactor, and the chlorine-containing compound and anhydrous hydrogen fluoride used as starting materials are introduced to the reactor can be given as one specific embodiment of the method of the present invention.

The reactor is preferably made of a material resistant to the corrosive action of hydrogen fluoride, such as Hastelloy, Inconel, Monel, or the like.

The lower limit of the reaction temperature is not particularly limited because a lower reaction temperature is advantageous in terms of less decomposition of the starting materials and the products. However, if the temperature is too low, the conversion of the chlorine-containing compound tends to decrease. For this reason, the reaction temperature is preferably 200° C. or more, and more preferably 220° C. or more.

Regarding the upper limit of the reaction temperature, an excessively high reaction temperature is not preferable because an excessively high reaction temperature notably decreases catalytic activity due to decomposition of the starting materials, and easily causes formation of $C_1$, $C_2$ compounds, and isomers, such as $CF_3CH$=$CHF$ and $CF_3CH$=$CHCl$, as by-products. For this reason, the reaction temperature is preferably about 400° C. or less. In particular, the reaction temperature in the trifluoropropene-producing reaction step is preferably about 200 to about 380° C.

The pressure during the reaction is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Furthermore, the reaction may be performed under increased pressure within a range in which the starting materials do not liquefy.

There is no limitation on the contact time. For example, the contact time, which is represented by $W/F_0$, is preferably adjusted to about 0.5 to about 50 g·sec/mL, and more preferably about 1 to about 20 g·sec/mL. $W/F_0$ is the ratio of the catalyst amount W(g) to the total flow rate $F_0$ (flow rate at 0° C., 0.1013 MPa: cc/sec) of the starting material gases supplied to the reaction system.

The starting materials may be supplied to the reactor as is, or a gas that is inert to the starting materials and catalyst, such as nitrogen, helium, or argon, may be present together with the starting materials. The concentration of the inert gas is about 0 to about 80 mol % based on the amount of the gaseous components introduced into the reactor.

Further, when the reaction is performed in a gas phase in the presence of a catalyst, one or both of oxygen and chlorine may be supplied to the reactor together with the starting materials to maintain catalytic activity for a long period of time. This enables suppression of a decrease in catalytic activity.

The inert gas, oxygen, and/or chlorine may be added in either the trifluoropropene-producing step or the below-described tetrafluoropropene-producing procedure, or in both. When the tetrafluoropropene-producing procedure is performed in two steps, the inert gas, oxygen, and/or chlorine may be added in any of the hydrogen fluoride addition step and the dehydrochlorination step.

(2) Tetrafluoropropene-Producing Procedure

The tetrafluoropropene-producing procedure is a procedure for obtaining 2,3,3,3-tetrafluoropropene or 2-chloro-1,1,1,2-tetrafluoropropane, which is a precursor of 2,3,3,3-tetrafluoropropene, from the 2-chloro-3,3,3-trifluoropropene obtained in the trifluoropropene-producing step.

The reaction for obtaining 2,3,3,3-tetrafluoropropene from 2-chloro-3,3,3-trifluoropropene can be performed by a method in which 2-chloro-3,3,3-trifluoropropene is reacted with anhydrous hydrogen fluoride in a gas phase in the presence of a fluorination catalyst to obtain 2,3,3,3-tetrafluoropropene (single-step method); or a method in which hydrogen fluoride is added to 2-chloro-3,3,3-trifluoropropene to obtain 2-chloro-1,1,1,2-tetrafluoropropane, and 2,3,3,3-tetrafluoropropene is obtained by dehydrochlorination of the 2-chloro-1,1,1,2-tetrafluoropropane (two-step method).

These methods are described in detail below.

(a) Single-Step Method

In the single-step method, 2-chloro-3,3,3-trifluoropropene is reacted with anhydrous hydrogen fluoride in a gas phase in the presence of a fluorination catalyst while heating to obtain 2,3,3,3-tetrafluoropropene according to the following reaction formula.

$$CF_3CCl=CH_2+HF\rightarrow CF_3CF=CH_2+HCl$$

The fluorination reaction in the tetrafluoropropene-producing reaction in the single-step method is performed in the presence of a fluorination catalyst. Examples of usable fluorination catalysts include known catalysts that are active in a fluorination reaction with hydrogen fluoride. For example, metal oxides and fluorinated metal oxides, such as chromium oxide, fluorinated chromium oxide, aluminum oxide, and fluorinated aluminum oxide, can be used. Other examples of usable fluorination catalysts are metal fluorides, such as $MgF_2$, $TaF_5$, and $SbF_5$.

As chromium oxide and fluorinated chromium oxide among these, the same catalysts as used in the trifluoropropene-producing step described above can be used.

In the tetrafluoropropene-producing reaction procedure, 2-chloro-3,3,3-trifluoropropene may be reacted with hydrogen fluoride (HF) in a gas phase in the presence of the fluorination catalyst described above while heating.

The specific reaction method is not particularly limited. When a fraction, containing 2-chloro-3,3,3-trifluoropropene and anhydrous hydrogen fluoride, separated in the distillation step described below is circulated, the fraction may be further heated with a preheater together with anhydrous hydrogen fluoride that is newly supplied as required, and supplied to the reactor to allow a reaction to proceed in a gas phase.

The amount of hydrogen fluoride supplied in the tetrafluoropropene-producing reaction procedure is generally about 1 to about 50 mol, preferably about 5 to about 30 mol, and more preferably about 7 to about 15 mol, per mol of 2-chloro-3,3,3-trifluoropropene supplied to the reactor.

When the amount of hydrogen fluoride in the fraction, obtained in the distillation step described below, that contains 2-chloro-3,3,3-trifluoropropene is within the above range, a fluorination reaction in the tetrafluoropropene-producing reaction procedure can be performed by using only the products obtained in the distillation step without adding further hydrogen fluoride. When the amount of hydrogen fluoride contained in the reaction products obtained in the distillation step is larger than the above range, the reaction products may be used as starting materials for the tetrafluoropropene-producing reaction procedure after reducing the amount of hydrogen fluoride contained therein by a method such as distillation.

The selectivity of 2,3,3,3-tetrafluoropropene can be maintained in a desirable range by using anhydrous hydrogen fluoride within the above range in the presence of the fluorination catalyst described above.

The form of the reactor used in the tetrafluoropropene-producing reaction procedure is not particularly limited. Examples of usable reactors include adiabatic reactors containing a catalyst, multitubular reactors cooled using a heating medium, and the like. The reactor is preferably made of a material resistant to the corrosive action of hydrogen fluoride, such as Hastelloy, Inconel, Monel, or the like.

The reaction temperature, i.e., the temperature in the reactor, is generally about 200 to about 500° C., preferably about 300 to about 450° C., and more preferably about 350 to about 400° C. If the reaction temperature is higher than this range, the selectivity of 2,3,3,3-tetrafluoropropene undesirably decreases. If the reaction temperature is lower than this range, the conversion of the starting compound undesirably decreases.

The pressure during the reaction is not particularly limited, and the reaction may be performed under ordinary pressure or increased pressure. More specifically, the reaction in the present invention may be performed under atmospheric pressure (0.1 MPa), and may also be performed under an increased pressure of up to about 1.0 MPa.

The reaction time is not particularly limited. However, the contact time, which is represented by $W/F_0$, may be generally adjusted to the range of about 5 to about 20 g·sec/cc. $W/F_0$ is the ratio of the catalyst amount $W(g)$ to the total flow rate Fo (flow rate at 0° C., 0.1013 MPa: cc/sec) of the starting material gases supplied (total amount of 2-chloro-3,3,3-trifluoropropene and HF).

(b) Two-Step Method (i) In the first step of the two-step method, hydrogen fluoride is added to 2-chloro-3,3,3-trifluoropropene to produce 2-chloro-1,1,1,2-tetrafluoropropane.

Various methods for producing 2-chloro-1,1,1,2-tetrafluoropropane by adding hydrogen fluoride to 2-chloro-3,3,3-trifluoropropene are known (WO2011/56441, WO2009/018561, and the like). In the present invention, these known methods can be appropriately applied.

For example, hydrogen fluoride can be added to 2-chloro-3,3,3-trifluoropropene in a liquid phase to produce 2-chloro-1,1,1,2-tetrafluoropropane. This method can be performed by supplying 2-chloro-3,3,3-trifluoropropene together with an excess of hydrogen fluoride to a liquid phase reactor containing a hydrogen fluoride addition catalyst such as $SbCl_3$, $SbCl_5$, $SbF_5$, or the like. As the reaction conditions, known conditions may be appropriately applied. For example, the reaction temperature may be about 85° C.

A known method for producing 2-chloro-1,1,1,2-tetrafluoropropane by adding hydrogen fluoride to 2-chloro-3,3,3-trifluoropropene through a gas phase reaction is, for example, a method in which 2-chloro-3,3,3-trifluoropropene and an excess of hydrogen fluoride are allowed to pass through a reactor containing a $SbCl_5$ catalyst supported on carbon. Other examples of catalysts that can be used in the hydrogen fluoride addition reaction in a gas phase include chromium-based catalysts, such as chromium oxide and fluorinated chromium oxide. As the reaction conditions of the gas phase reaction, known conditions may be appropriately applied. For example, the reaction temperature may be within the range of about 50 to about 300° C.

In view of the apparatus configuration of the process, controllability, and the like, the reaction of addition of hydrogen fluoride to 2-chloro-3,3,3-trifluoropropene is preferably performed through a gas phase reaction.

2-chloro-1,1,1,2-tetrafluoropropane can be obtained by performing the above-described hydrogen fluoride addition reaction in the first step. Since 2-chloro-1,1,1,2-tetrafluoropropane can be converted into 2,3,3,3-tetrafluoropropene by performing the below-described dehydrochlorination reaction in the second step, it is a useful compound as a precursor of 2,3,3,3-tetrafluoropropene. Therefore, the reaction until the completion of the hydrogen fluoride addition in the first step can be defined as a method for producing 2-chloro-1,1,1,2-tetrafluoropropane.

Although the products of the first step do not contain hydrogen chloride, they are generally subjected to a distillation operation to separate useful materials and impurities from the products.

(ii) In the reaction of the second step, 2,3,3,3-tetrafluoropropene can be obtained by dehydrochlorination of the 2-chloro-1,1,1,2-tetrafluoropropane.

Various methods for dehydrochlorination of 2-chloro-1,1,1,2-tetrafluoropropane are known (WO2011/56441, WO2009/018561, and the like). In the present invention, these known methods can be appropriately applied.

For example, the dehydrochlorination reaction can be performed by supplying 2-chloro-1,1,1,2-tetrafluoropropane to a basic aqueous solution. Examples of basic aqueous solutions include aqueous NaOH solution, aqueous KOH solution, and the like. As the specific reaction conditions, known conditions may be appropriately applied.

As for dehydrochlorination of 2-chloro-1,1,1,2-tetrafluoropropane through a gas phase reaction, the method disclosed in WO2009/018561, for example, can be applied. This method can be performed by, for example, bringing 2-chloro-1,1,1,2-tetrafluoropropane into contact with a dehydrochlorination catalyst. Examples of catalysts include metal halides on carbon and/or metal, halogenated metal oxides on carbon and/or metal, and the like. As the reaction conditions of the gas phase reaction, known conditions may be appropriately applied. The reaction temperature may be within the range of, for example, about 200 to about 550° C.

In view of the apparatus configuration of the process, controllability, and the like, the dehydrochlorination of 2-chloro-1,1,1,2-tetrafluoropropane is preferably performed through a gas phase reaction.

(3) Distillation Step (i) In the method described above, in which the trifluoropropene-producing reaction and the tetrafluoropropene-producing reaction are performed, when the tetrafluoropropene-producing reaction is performed by the single-step method, 2,3,3,3-tetrafluoropropene can be obtained from the chlorine-containing compound as a starting material in two steps. When the tetrafluoropropene-producing reaction is performed by the two-step method, 2,3,3,3-tetrafluoropropene can be obtained from the chlorine-containing compound as a starting material in three steps.

In the method for producing 2,3,3,3-tetrafluoropropene of the present invention, which comprises these two steps or three steps, the reaction products of at least two of the steps are supplied to the same distillation apparatus to subject the reaction products to a separation operation simultaneously. In particular, in the method comprising three steps, the reaction products of all of the steps are preferably supplied to the same distillation apparatus to subject the products to a distillation operation simultaneously.

When the products of each reaction step are supplied to the distillation apparatus, the components obtained from the outlets of the reaction steps may be mixed before they are supplied to the distillation apparatus, or the components obtained from the outlets of the reaction steps may be separately introduced into the distillation apparatus from different desired positions, for example, separately introduced from a middle portion of the distillation column, the bottom of the distillation column, etc. When they are introduced from different positions of the distillation apparatus, the positions from which they are introduced are appropriately determined according to the composition of the components obtained from the outlet of each reaction step and the composition of each fraction obtained from the separation step.

When the reaction before supplying to the distillation step is a gas phase reaction, the components obtained from the outlet of the reactor can be supplied as is to the distillation step. When the reaction before supplying to the distillation step is a liquid phase reaction, volatile components can be continuously removed from the reactor and supplied to the distillation step. When the liquid phase portion is continuously removed and supplied to the separation step, a step of removing and collecting the catalyst contained in the liquid phase portion may be performed as a pretreatment step before the distillation step.

The distillation conditions in the distillation step may be conditions under which the products can be separated into a hydrogen chloride-containing fraction and a fraction substantially free of hydrogen chloride. In this case, to almost completely remove hydrogen chloride contained in the reaction products, the hydrogen chloride-containing fraction preferably contains substantially the same amount of hydrogen chloride as the amount of hydrogen chloride introduced into the distillation step.

If necessary, the hydrogen chloride-free fraction separated in the distillation step may be further subjected to a crude purification treatment step (separation step), such as distillation, to separate the unreacted starting materials usable in the reaction steps, intermediates, hydrogen fluoride, and the like, after which these may be individually recycled to any of the reaction steps.

After the hydrogen chloride-containing fraction is subjected to a step of removing hydrogen chloride, it may also be subjected to a separation step to separate the unreacted starting materials usable in the reaction steps, intermediates, hydrogen fluoride, and the like, after which these may be individually recycled to any of the reaction steps.

Examples of intermediates as used herein include compounds produced as a result of reactions such as replacement of chlorine atom(s) of the starting material chlorine-containing compound by fluorine, hydrogen fluoride addition, dehydrochlorination, or dehydrofluorination. Although they depend on the step used and the reaction conditions thereof, specific examples include 1,1,2,3-tetrachloro-1-fluoropropane (HCFC-241db), 1,1,2-trichloro-1,3-difluoropropane (HCFC-242dc), 2,3,3-trichloro-3-fluoropropene (HCFO-1231xf), 2,3-dichloro-3,3-difluoropropene (HCFO-1232xf), 1,1,1,2,2-pentafluoropropane (HFC-245cb), and the like.

When the desired 2,3,3,3-tetrafluoropropene is contained in the hydrogen chloride-containing fraction and/or the fraction free of hydrogen chloride, the hydrogen chloride-containing fraction and/or the fraction free of hydrogen chloride may be subjected to a step of collecting 2,3,3,3-tetrafluoropropene, and the components other than 2,3,3,3-tetrafluoropropene can be recycled to necessary steps.

When the fractions obtained in the distillation step are recycled, an acid removal step, a moisture removal step, a crude purification step, such as distillation, or the like may be performed if necessary. The treatment conditions of each step may be appropriately set depending on the components to be separated.

For example, in the method for producing 2,3,3,3-tetrafluoropropene comprising two steps, specific distillation conditions in the distillation step may be conditions under which 2-chloro-3,3,3-trifluoropropene, hydrogen fluoride, and the like can be separated as high-boiling-point components, and 2,3,3,3-tetrafluoropropene, hydrogen chloride, and the like can be separated as low-boiling-point components. Of the fractions thus separated, the fraction containing 2-chloro-3,3,3-trifluoropropene, hydrogen fluoride, and the like, which are high-boiling-point components, may further be, if necessary, subjected to distillation treatment or the like to separate 2-chloro-3,3,3-trifluoropropene, 1,1,1,2,2-pentafluoropropane, which is an intermediate of 2-chloro-3,3,3-trifluoropropene, hydrogen fluoride, and the like. These components can be used as starting materials in the tetrafluoropropene-producing procedure. Hydrogen fluoride contained in an excess amount can be recycled, for example, as a starting material in the trifluoropropene-producing step.

The fraction containing 2,3,3,3-tetrafluoropropene, hydrogen chloride, and the like separated as low-boiling-point components can further be subjected to any purification step such as single- or multi-stage distillation, liquid separation, extraction, or extractive distillation, to separate and collect 2,3,3,3-tetrafluoropropene. For example, when a distillation operation is performed as a separation means, a single- or multi-stage distillation operation can be carried out to collect high-purity 2,3,3,3-tetrafluoropropene from the bottom of the final distillation column or a middle portion of the final distillation column. Hydrogen chloride can be collected from the top of the distillation column and recycled for the desired purpose. Other organic components contained in the hydrogen chloride-containing fraction are chlorine-containing fluorides, which can be used as intermediate materials in the reaction steps. Thus, these organic components can be separated in the step of collecting 2,3,3,3-tetrafluoropropene and recycled to the desired reaction steps.

(ii) When the tetrafluoropropene-producing procedure is performed by the two-step method, i.e., when hydrogen fluoride is added to 2-chloro-3,3,3-trifluoropropene to obtain 2-chloro-1,1,1,2-tetrafluoropropane, and then a dehydrochlorination reaction is performed to obtain 2,3,3,3-tetrafluoropropene, the reactions of the two steps can be used as a method for producing 2,3,3,3-tetrafluoropropene. In this case, as 2-chloro-3,3,3-trifluoropropene, 2-chloro-3,3,3-trifluoropropene obtained as a product of the trifluoropropene-producing step described above or 2-chloro-3,3,3-trifluoropropene obtained by any other method may be used.

In this method, the reaction products of the step of addition of hydrogen fluoride to 2-chloro-3,3,3-trifluoropropene and the reaction products of the step of dehydrochlorination of 2-chloro-1,1,1,2-tetrafluoropropane may be introduced into the same distillation apparatus to perform a distillation operation simultaneously. This method makes it possible to simultaneously perform collection of useful materials from the reaction products of the step of addition of hydrogen fluoride as well as removal of hydrogen chloride and collection of useful materials from the reaction products of the dehydrochlorination step by using a single distillation apparatus. Also in this case, the unreacted starting materials, intermediates, hydrogen fluoride, and the like contained in each fraction can be, if necessary, recycled to any of the steps after being subjected to a separation step.

(iii) As stated above, in the tetrafluoropropene-producing procedure performed in two reaction steps, 2-chloro-1,1,1,2-tetrafluoropropane, which is useful as a precursor of 2,3,3,3-tetrafluoropropene, can be obtained by performing the hydrogen fluoride addition reaction in the first step.

Thus, the method in which 2-chloro-3,3,3-trifluoropropene is obtained through the trifluoropropene-producing step, and then hydrogen fluoride is added to the obtained 2-chloro-3,3,3-trifluoropropene is useful as a method for producing 2-chloro-1,1,1,2-tetrafluoropropane.

Also in this method, the reaction products of the trifluoropropene-producing step and the reaction products of the hydrogen fluoride addition step may be introduced into the same distillation apparatus to perform a distillation operation simultaneously. Thereby, the method makes it possible to simultaneously perform removal of hydrogen chloride from the products of the trifluoropropene-producing step and collection of useful components by using a single distillation apparatus. Also in this case, the unreacted starting materials, intermediates, hydrogen fluoride, and the like contained in each fraction may be, if necessary, recycled to any of the steps after being subjected to a separation step.

Advantageous Effects of Invention

The method of the present invention makes it possible to efficiently produce 2,3,3,3-tetrafluoropropene or 2-chloro-1,1,1,2-tetrafluoropropane, which is a precursor of 2,3,3,3-tetrafluoropropene, using at least one chlorine-containing compound selected from the group consisting of 1,1,1,2,3-pentachloropropane, 2,3-dichloro-1,1,1-trifluoropropane, and 1,1,2,3-tetrachloropropene as a starting material, with reduced energy and equipment costs in an economically advantageous manner.

Further, the present invention also makes it possible to perform a method for producing 2,3,3,3-tetrafluoropropene by adding hydrogen fluoride to 2-chloro-3,3,3-trifluoropropene to obtain 2-chloro-1,1,1,2-tetrafluoropropane and then conducting a dehydrochlorination reaction, with reduced energy and equipment costs in an economically advantageous manner.

DESCRIPTION OF EMBODIMENTS

The present invention is described in more detail below with reference to Examples.

EXAMPLE 1

Figure 2:
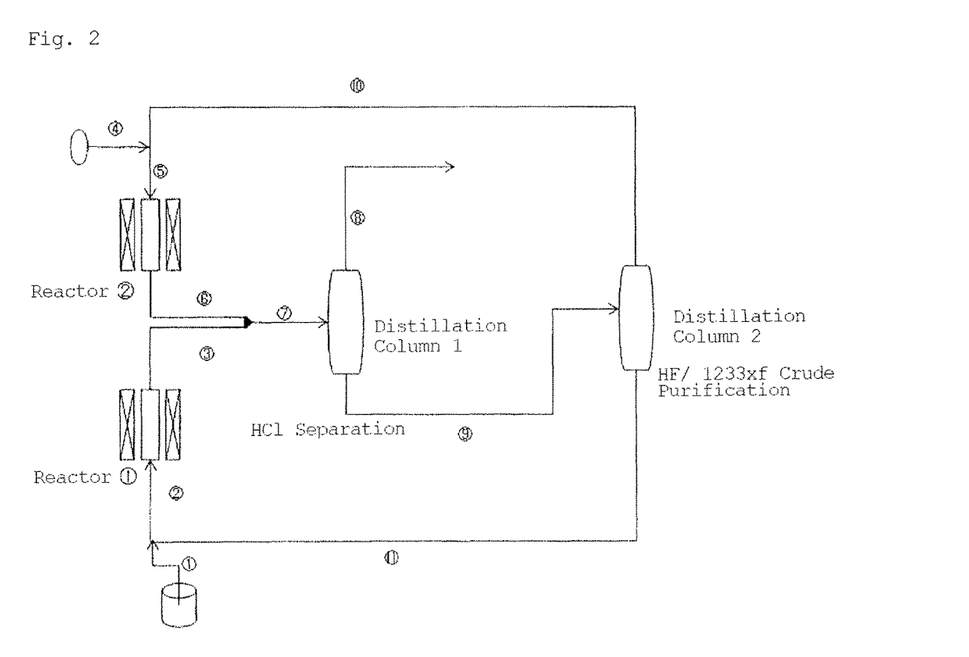
FIG. 2 is a flow diagram of the reaction process in Examples 1 to 3.

According to the flow diagram shown in FIG. 2, 2,3,3,3-tetrafluoropropene was produced using 1,1,1,2,3-pentachloropropane as a starting material by a process comprising the trifluoropropene-producing step and the tetrafluoropropene-producing procedure (single-step method).

A Hastelloy reactor with a capacity of 1.5 L was used as a reactor for the trifluoropropene-producing step (reactor 1), and 1.3 kg of chromium oxide containing $CrO_2$ as a main component was placed in the reactor as a catalyst. A Hastelloy reactor with a capacity of 9 L was used as a reactor for the tetrafluoropropene-producing procedure (reactor 2), and 7.7 kg of chromium oxide containing $CrO_2$ as a main component was placed in the reactor as a catalyst.

As a pretreatment before the use of these catalysts for the corresponding reactions, fluorination treatment was performed by passing anhydrous hydrogen fluoride diluted with nitrogen through the reactors and raising the temperature of each reactor from 200° C. to 360° C. The fluorinated catalysts were used for the corresponding reactions without being removed.

While allowing nitrogen to flow into the reactors, the reactors and preheaters were each heated with an electric furnace. After predetermined temperatures were reached, an operation of the process shown in FIG. 2 started.

The operating conditions of the reactor for the trifluoropropene-producing reaction step (reactor 1) were as follows: a pressure of 0.1 MPa and a temperature of 300° C. The operating conditions of the reactor for the tetrafluoropropene-producing reaction procedure (reactor 2) were as follows: a pressure of 0.1 MPa and a temperature of 365° C. The operating conditions of distillation column 1 (HCl separation step) were as follows: a pressure of 0.75 MPa, a column top temperature of −13° C., and a column bottom temperature of 92° C. Further, a distillation operation at a pressure of 0.75 MPa, a column top temperature of 87° C., and a column bottom temperature of 90° C. was performed using distillation column 2 as a crude purification step.

50 hours after the operation of the process started, the composition of components in each step of the reaction process was analyzed using gas chromatography. Table 1 shows the operating conditions of each step of the reaction process. Table 2 shows the results of the analysis. The circled numbers shown in Table 2 correspond to the numbers of the steps of the reaction process shown in FIG. 2.

The structure of each product is as follows:

$CF_3CF=CH_2$ (HFO-1234yf)

$CF_3CF_2CH_3$ (HFC-245cb)

$CF_3CCl=CH_2$ (HCFO-1233xf)

$CCl_3CHClCH_2Cl$ (HCC-240db)

TABLE 1

| Reaction Step | Reaction Temperature (° C.) | | Pressure (MPa) |
| --- | --- | --- | --- |
| Reactor 1 | 300 | | 0.1 |
| Reactor 2 | 365 | | 0.1 |
| Distillation Step | Column Top Temperature (° C.) | Column Bottom Temperature (° C.) | Pressure (MPa) |
| Distillation Column 1 (HCl Separation) | −13 | 92 | 0.75 |
| Distillation Column 2 (Crude Purification) | 87 | 90 | 0.75 |

TABLE 2

| | $O_2$ (kmol/hr) | HCl (kmol/hr) | HF (kmol/hr) | 1234yf (kmol/hr) | 245cb (kmol/hr) | 1233xf (kmol/hr) | 240db (kmol/hr) |
|---|---|---|---|---|---|---|---|
| ① | 0.00 | 0.00 | 4.50 | 0.00 | 0.00 | 0.00 | 1.14 |
| ② | 0.00 | 0.00 | 23.9 | 0.00 | 0.00 | 0.08 | 1.14 |
| ③ | 0.00 | 4.52 | 20.5 | 0.00 | 0.00 | 1.21 | 0.01 |
| ④ | 1.02 | 0.00 | 0.00 | 0.00 | 0.00 | 0.00 | 0.00 |
| ⑤ | 1.02 | 0.00 | 145 | 0.01 | 0.34 | 7.14 | 0.00 |
| ⑥ | 1.02 | 1.13 | 144 | 1.13 | 0.34 | 6.01 | 0.00 |
| ⑦ | 1.02 | 5.65 | 164 | 1.13 | 0.34 | 7.22 | 0.01 |
| ⑧ | 1.02 | 5.65 | 0.00 | 1.12 | 0.00 | 0.00 | 0.00 |
| ⑨ | 0.00 | 0.00 | 164 | 0.01 | 0.34 | 7.22 | 0.00 |
| ⑩ | 0.00 | 0.00 | 145 | 0.01 | 0.34 | 7.14 | 0.00 |
| ⑪ | 0.00 | 0.00 | 19.4 | 0.00 | 0.00 | 0.08 | 0.01 |

As is clear from Table 2, it can be confirmed that separation of hydrogen chloride and collection of 2,3,3,3-tetrafluoropropene from the products can be carried out using a single distillation apparatus by supplying the components obtained from the outlet of the reactor for the trifluoropropene-producing reaction step (reactor 1) and the components obtained from the outlet of the reactor for the tetrafluoropropene-producing reaction procedure (reactor 2) to the same distillation apparatus to perform a distillation operation. Further, the results show that the unreacted starting material, intermediates, hydrogen fluoride, and the like can effectively be used by subjecting the fraction free of hydrogen chloride to a crude purification (distillation) operation.

EXAMPLE 2

According to the flow diagram shown in FIG. 2, 2,3,3,3-tetrafluoropropene was produced using 2,3-dichloro-1,1,1-trifluoropropane (HCFC-243db) as a starting material by a process comprising the trifluoropropene-producing step and the tetrafluoropropene-producing procedure (single-step method).

A Hastelloy reactor with a capacity of 1.3 L was used as a reactor for the trifluoropropene-producing step (reactor 1), and 1.1 kg of chromium oxide containing $CrO_2$ as a main component was placed in the reactor as a catalyst. A Hastelloy reactor with a capacity of 12 L was used as a reactor for the tetrafluoropropene-producing procedure (reactor 2), and 10 kg of chromium oxide containing $CrO_2$ as a main component was placed in the reactor as a catalyst.

Fluorination treatment of the catalysts before the reactions and heating of the reactors were performed in the same manner as in Example 1. Thereafter, an operation of the process started under the operating conditions shown in Table 3. The composition of components in each step of the reaction process was analyzed using gas chromatography in the same manner as in Example 1. Table 4 shows the results.

TABLE 3

| Reaction Step | Reaction Temperature (° C.) | Pressure (MPa) |
|---|---|---|
| Reactor 1 | 300 | 0.1 |
| Reactor 2 | 365 | 0.1 |

| Distillation Step | Column Top Temperature (° C.) | Column Bottom Temperature (° C.) | Pressure (MPa) |
|---|---|---|---|
| Distillation Column 1 (HCl Separation) | −1.4 | 92 | 0.75 |
| Distillation Column 2 (Crude Purification) | 86 | 88 | 0.75 |

TABLE 4

| | $O_2$ (kmol/hr) | HCl (kmol/hr) | HF (kmol/hr) | 1234yf (kmol/hr) | 245cb (kmol/hr) | 1233xf (kmol/hr) | 243db (kmol/hr) |
|---|---|---|---|---|---|---|---|
| ① | 0.00 | 0.00 | 1.50 | 0.00 | 0.00 | 0.00 | 1.82 |
| ② | 0.00 | 0.00 | 19.6 | 0.00 | 0.00 | 0.13 | 1.82 |
| ③ | 0.00 | 1.82 | 19.6 | 0.00 | 0.00 | 1.94 | 0.01 |
| ④ | 1.02 | 0.00 | 0.00 | 0.00 | 0.00 | 0.00 | 0.00 |
| ⑤ | 1.02 | 0.00 | 134 | 0.01 | 0.46 | 11.4 | 0.00 |
| ⑥ | 1.02 | 1.82 | 132 | 1.83 | 0.46 | 9.55 | 0.00 |
| ⑦ | 1.02 | 3.64 | 152 | 1.83 | 0.46 | 11.5 | 0.01 |
| ⑧ | 1.02 | 3.64 | 0.00 | 1.82 | 0.00 | 0.00 | 0.00 |
| ⑨ | 0.00 | 0.00 | 152 | 0.01 | 0.46 | 11.5 | 0.01 |
| ⑩ | 0.00 | 0.00 | 134 | 0.01 | 0.46 | 11.4 | 0.00 |
| ⑪ | 0.00 | 0.00 | 18.1 | 0.00 | 0.00 | 0.13 | 0.01 |

As is clear from Table 4, also when 2,3-dichloro-1,1,1-trifluoropropane is used as a starting material, it can be confirmed that separation of hydrogen chloride and collection of 2,3,3,3-tetrafluoropropene from the products can be carried out using a single distillation apparatus by supplying the components obtained from the outlet of the reactor for the trifluoropropene-producing reaction step (reactor 1) and the components obtained from the outlet of the reactor for the tetrafluoropropene-producing reaction procedure (reactor 2) to the same distillation apparatus to perform a distillation operation. Further, the results show that the unreacted starting material, intermediates, hydrogen fluoride, and the like can effectively be used by subjecting the fraction free of hydrogen chloride to a crude purification (distillation) operation.

EXAMPLE 3

According to the flow diagram shown in FIG. 2, 2,3,3,3-tetrafluoropropene was produced using 1,1,2,3-tetrachloropropene as a starting material by a process comprising the trifluoropropene-producing step and the tetrafluoropropene-producing procedure (single-step method).

A Hastelloy reactor with a capacity of 1.3 L was used as a reactor for the trifluoropropene-producing step (reactor 1), and 1.1 kg of chromium oxide containing $CrO_2$ as a main component was placed in the reactor as a catalyst. A Hastelloy reactor with a capacity of 7.7 L was used as a reactor for the tetrafluoropropene-producing procedure (reactor 2), and 6.4 kg of chromium oxide containing $CrO_2$ as a main component was placed in the reactor as a catalyst.

Fluorination treatment of the catalysts before the reactions and heating of the reactors were performed in the same manner as in Example 1. Thereafter, an operation of the process started under the operating conditions shown in Table 5. The composition of components in each step of the reaction process was analyzed using gas chromatography in the same manner as in Example 1. Table 6 shows the results.

TABLE 5

| Reaction Step | Reaction Temperature (° C.) | Pressure (MPa) |
| --- | --- | --- |
| Reactor 1 | 300 | 0.1 |
| Reactor 2 | 365 | 0.1 |

| Distillation Step | Column Top Temperature (° C.) | Column Bottom Temperature (° C.) | Pressure (MPa) |
| --- | --- | --- | --- |
| Distillation Column 1 (HCl Separation) | −8.9 | 92 | 0.75 |
| Distillation Column 2 (Crude Purification) | 88 | 89 | 0.75 |

TABLE 6

| | $O_2$ (kmol/hr) | HCl (kmol/hr) | HF (kmol/hr) | 1234yf (kmol/hr) | 245cb (kmol/hr) | 1233xf (kmol/hr) | 1230xa (kmol/hr) |
| --- | --- | --- | --- | --- | --- | --- | --- |
| ① | 0.00 | 0.00 | 7.00 | 0.00 | 0.00 | 0.00 | 1.82 |
| ② | 0.00 | 0.00 | 27.2 | 0.00 | 0.00 | 0.13 | 1.82 |
| ③ | 0.00 | 5.43 | 21.8 | 0.00 | 0.00 | 1.94 | 0.01 |
| ④ | 1.02 | 0.00 | 0.00 | 0.00 | 0.00 | 0.00 | 0.00 |
| ⑤ | 1.02 | 0.00 | 167 | 0.01 | 0.46 | 11.4 | 0.00 |
| ⑥ | 1.02 | 1.82 | 165 | 1.83 | 0.46 | 9.55 | 0.00 |
| ⑦ | 1.02 | 7.25 | 187 | 1.83 | 0.46 | 11.5 | 0.01 |
| ⑧ | 1.02 | 7.25 | 0.00 | 1.82 | 0.00 | 0.00 | 0.00 |
| ⑨ | 0.00 | 0.00 | 187 | 0.01 | 0.46 | 11.5 | 0.01 |
| ⑩ | 0.00 | 0.00 | 167 | 0.01 | 0.46 | 11.4 | 0.00 |
| ⑪ | 0.00 | 0.00 | 20.2 | 0.00 | 0.00 | 0.13 | 0.01 |

As is clear from Table 6, also when 1,1,2,3-tetrachloropropene is used as a starting material, it can be confirmed that separation of hydrogen chloride and collection of 2,3,3,3-tetrafluoropropene from the products can be carried out using a single distillation apparatus by supplying the components obtained from the outlet of the reactor for the trifluoropropene-producing reaction step (reactor 1) and the components obtained from the outlet of the reactor for the tetrafluoropropene-producing reaction procedure (reactor 2) to the same distillation apparatus to perform a distillation operation. Further, the results show that the unreacted starting material, intermediates, hydrogen fluoride, and the like can effectively be used by subjecting the fraction free of hydrogen chloride to a crude purification (distillation) operation.

EXAMPLE 4

Figure 3:
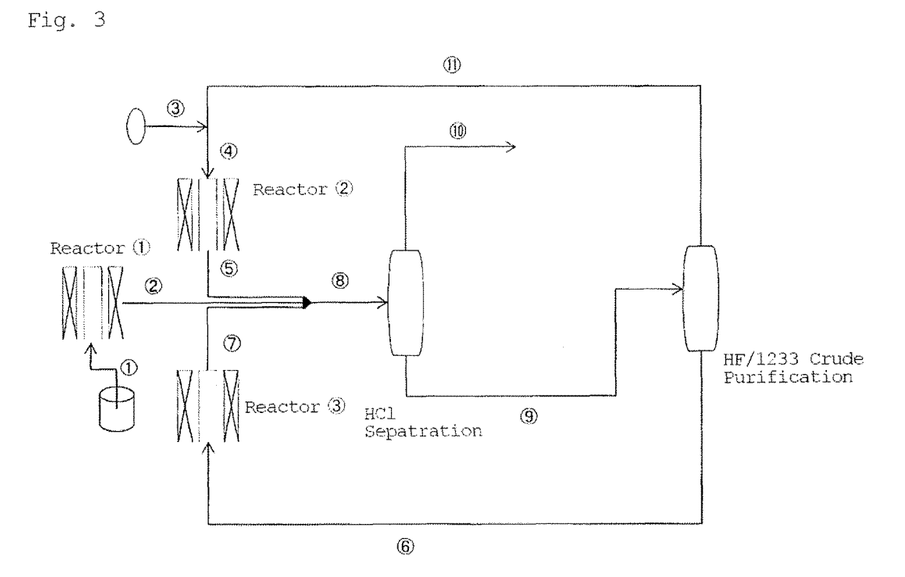
FIG. 3 is a flow diagram of the reaction process in Examples 4 and 5.

According to the flow diagram shown in FIG. 3, 2,3,3,3-tetrafluoropropene was produced by a process comprising the trifluoropropene-producing step in which 2-chloro-3,3,3-trifluoropropene is obtained using 1,1,2,3-tetrachloropropene as a starting material, and comprising the tetrafluoropropene-producing procedure performed in two reaction steps in which hydrogen fluoride is added to the 2-chloro-3,3,3-trifluoropropene obtained in the trifluoropropene-producing step to produce 2-chloro-1,1,1,2-tetrafluoropropane and then a dehydrochlorination reaction is performed to produce 2,3,3,3-tetrafluoropropene.

A Hastelloy reactor with a capacity of 0.5 L was used as a reactor for the trifluoropropene-producing step (reactor 1), and 0.4 kg of chromium oxide containing $CrO_2$ as a main component was placed in the reactor as a catalyst. A Hastelloy reactor with a capacity of 2.5 L was used as a reactor for the step of addition of hydrogen fluoride to 2-chloro-3,3,3-trifluoropropene (reactor 2), and 2.1 kg of chromium oxide containing $CrO_2$ as a main component was placed in the reactor as a catalyst. A Hastelloy reactor with a capacity of 2.0 L was used as a reactor for the step of dehydrochlorination of 2-chloro-1,1,1,2-tetrafluoropropane (reactor 3), and 1.6 kg of chromium oxide containing $CrO_2$ as a main component was placed in the reactor as a catalyst.

Fluorination treatment of the catalysts before the reactions and heating of the reactors were performed in the same manner as in Example 1. Thereafter, an operation of the process started under the operating conditions shown in Table 7. The composition of components in each step of the reaction process was analyzed using gas chromatography in the same manner as in Example 1. Table 8 shows the results.

TABLE 7

| Reaction Step | Reaction Temperature (° C.) | Pressure (MPa) |
| --- | --- | --- |
| Reactor 1 | 300 | 0.1 |
| Reactor 2 | 365 | 0.1 |
| Reactor 3 | 365 | 0.1 |

TABLE 7-continued

| Distillation Step | Column Top Temperature (° C.) | Column Bottom Temperature (° C.) | Pressure (MPa) |
|---|---|---|---|
| Distillation Column 1 (HCl Separation) | −1.8 | 92 | 0.75 |
| Distillation Column 2 (Crude Purification) | 84 | 96 | 0.75 |

TABLE 8

| | HCl (kmol/hr) | HF (kmol/hr) | 1234yf (kmol/hr) | 1233xf (kmol/hr) | 1230xa (kmol/hr) | 244bb (kmol/hr) |
|---|---|---|---|---|---|---|
| ① | 0.00 | 9.00 | 0.00 | 0.00 | 2.97 | 0.00 |
| ② | 8.91 | 0.09 | 0.00 | 2.97 | 0.00 | 0.00 |
| ③ | 0.00 | 2.70 | 0.00 | 0.00 | 0.00 | 0.00 |
| ④ | 0.00 | 12.6 | 0.02 | 14.3 | 0.00 | 9.66 |
| ⑤ | 0.00 | 0.00 | 0.02 | 1.66 | 0.00 | 22.3 |
| ⑥ | 0.00 | 9.50 | 0.00 | 0.00 | 0.00 | 13.6 |
| ⑦ | 2.85 | 19.3 | 2.85 | 9.80 | 0.00 | 0.95 |
| ⑧ | 11.8 | 19.4 | 2.88 | 14.3 | 0.00 | 23.3 |
| ⑨ | 0.00 | 19.4 | 0.02 | 14.3 | 0.00 | 23.3 |
| ⑩ | 11.8 | 0.00 | 2.86 | 0.00 | 0.00 | 0.00 |
| ⑪ | 0.00 | 9.90 | 0.02 | 14.3 | 0.00 | 9.66 |

As is clear from Table 8, also in the method comprising three steps in which the tetrafluoropropene-producing reaction procedure is performed in two steps, it can be confirmed that separation of hydrogen chloride and collection of 2,3,3,3-tetrafluoropropene from the products can be carried out using a single distillation apparatus by supplying the components obtained from the outlet of the reactor for the trifluoropropene-producing reaction step (reactor 1), the components obtained from the outlet of the reactor for the step of addition of hydrogen fluoride to 2-chloro-3,3,3-trifluoropropene (reactor 2), and the components obtained from the outlet of the reactor for the step of dehydrochlorination of 2-chloro-1,1,1,2-tetrafluoropropane (reactor 3) to the same distillation apparatus to perform a distillation operation. Further, the results show that the unreacted starting material, intermediates, hydrogen fluoride, and the like can effectively be used by subjecting the fraction free of hydrogen chloride to a crude purification (distillation) operation.

EXAMPLE 5

According to the flow diagram shown in FIG. 3, 2,3,3,3-tetrafluoropropene was produced using 2,3-dichloro-1,1,1-trifluoropropane as a starting material. The tetrafluoropropene-producing procedure was carried out in the same manner as in Example 4 in two steps in which hydrogen fluoride is added to the 2-chloro-3,3,3-trifluoropropene obtained in the trifluoropropene-producing step to produce 2-chloro-1,1,1,2-tetrafluoropropane, and then a dehydrochlorination reaction is performed to produce 2,3,3,3-tetrafluoropropene.

A Hastelloy reactor with a capacity of 0.12 L was used as a reactor for the trifluoropropene-producing step (reactor 1), and 0.1 kg of chromium oxide containing $CrO_2$ as a main component was placed in the reactor as a catalyst. A Hastelloy reactor with a capacity of 1.7 L was used as a reactor for the step of addition of hydrogen fluoride to 2-chloro-3,3,3-trifluoropropene (reactor 2), and 1.4 kg of chromium oxide containing $CrO_2$ as a main component was placed in the reactor as a catalyst. A Hastelloy reactor with a capacity of 1.7 L was used as a reactor for the step of dehydrochlorination of 2-chloro-1,1,1,2-tetrafluoropropane (reactor 3), and 1.4 kg of chromium oxide containing $CrO_2$ as a main component was placed in the reactor as a catalyst.

Fluorination treatment of the catalysts before the reactions and heating of the reactors were performed in the same manner as in Example 1. Thereafter, an operation of the process started under the operating conditions shown in Table 9. The composition of components in each step of the reaction process was analyzed using gas chromatography in the same manner as in Example 1. Table 10 shows the results.

TABLE 9

| Reaction Step | Reaction Temperature (° C.) | Pressure (MPa) |
|---|---|---|
| Reactor 1 | 300 | 0.1 |
| Reactor 2 | 365 | 0.1 |
| Reactor 3 | 365 | 0.1 |

| Distillation Step | Column Top Temperature (° C.) | Column Bottom Temperature (° C.) | Pressure (MPa) |
|---|---|---|---|
| Distillation Column 1 (HCl Separation) | 8.3 | 92 | 0.75 |
| Distillation Column 2 (Crude Purification) | 86 | 96 | 0.75 |

TABLE 10

| | HCl (kmol/hr) | HF (kmol/hr) | 1234yf (kmol/hr) | 1233xf (kmol/hr) | 244bb (kmol/hr) | 243db (kmol/hr) |
|---|---|---|---|---|---|---|
| ① | 0.00 | 0.00 | 0.00 | 0.00 | 0.00 | 3.00 |
| ② | 3.00 | 0.00 | 0.00 | 3.00 | 0.00 | 0.00 |
| ③ | 0.00 | 2.60 | 0.00 | 0.00 | 0.00 | 0.00 |
| ④ | 0.00 | 13.0 | 0.03 | 12.5 | 11.7 | 0.00 |
| ⑤ | 0.00 | 0.50 | 0.03 | 0.00 | 24.2 | 0.00 |
| ⑥ | 0.00 | 10.2 | 0.00 | 0.00 | 13.4 | 0.00 |
| ⑦ | 2.82 | 19.9 | 2.80 | 9.70 | 0.90 | 0.00 |
| ⑧ | 5.82 | 20.4 | 2.83 | 12.7 | 25.1 | 0.00 |
| ⑨ | 0.00 | 20.6 | 0.03 | 12.5 | 25.1 | 0.00 |
| ⑩ | 5.82 | 0.02 | 2.80 | 0.20 | 0.00 | 0.00 |
| ⑪ | 0.00 | 10.4 | 0.03 | 12.5 | 11.7 | 0.00 |

As is clear from Table 10, also in the method for producing 2,3,3,3-tetrafluoropropene using 2,3-dichloro-1,1,1-trifluoropropane as a starting material in three steps in which the tetrafluoropropene-producing reaction procedure is performed in two steps, it can be confirmed that separation of hydrogen chloride and collection of 2,3,3,3-tetrafluoropropene from the products can be carried out using a single distillation apparatus by supplying the components obtained from the outlet of the reactor for the trifluoropropene-producing reaction step (reactor 1), the components obtained from the outlet of the reactor for the step of addition of hydrogen fluoride to 2-chloro-3,3,3-trifluoropropene (reactor 2), and the components obtained from the outlet of the reactor for the step of dehydrochlorination of 2-chloro-1,1,1,2-tetrafluoropropane (reactor 3) to the same distillation apparatus to perform a distillation operation. Further, the results show that the unreacted starting material, intermediates, hydrogen fluoride, and the like can effectively be used by subjecting the fraction free of hydrogen chloride to a crude purification (distillation) operation.

COMPARATIVE EXAMPLE 1

As a comparative example, 2,3,3,3-tetrafluoropropene was produced using 1,1,1,2,3-pentachloropropane as a starting material by the general process shown in FIG. 1.

More specifically, after the trifluoropropene-producing step in which 2-chloro-3,3,3-trifluoropropene is obtained using 1,1,1,2,3-pentachloropropane as a starting material was performed in reactor 1, a distillation operation for separating HCl, which is a by-product, was carried out in a distillation column A. Subsequently, a distillation operation for separating unreacted 1,1,1,2,3-pentachloropropane and 2-chloro-3,3,3-trifluoropropene, which is a reaction product, was performed using a distillation column B as a crude purification step. The tetrafluoropropene-producing procedure in which 2-chloro-3,3,3-trifluoropropene is fluorinated to produce 2,3,3,3-tetrafluoropropene was then performed in reactor 2. The components obtained from the outlet of the reactor of the tetrafluoropropene-producing procedure was supplied to a distillation column C, and a distillation operation was carried out to separate the components into a column top fraction containing HCl and 2,3,3,3-tetrafluoropropene as main components, and a column bottom fraction containing HF and 2-chloro-3,3,3-trifluoropropene as main components. The column bottom fraction was recycled to the reactor 2. The column top fraction can be subjected to any purification step to obtain 2,3,3,3-tetrafluoropropene.

A Hastelloy reactor with a capacity of 1.2 L was used as a reactor for the trifluoropropene-producing step (reactor 1), and 1.0 kg of chromium oxide containing $CrO_2$ as a main component was placed in the reactor as a catalyst.

The operating conditions in the distillation column A (HCl separation step) were as follows: a pressure of 0.75 MPa, a column top temperature of −31° C., and a column bottom temperature of 91° C. The operating conditions in the distillation column B (crude purification step) were as follows: a pressure of 0.75 MPa, a column top temperature of 65° C., and a column bottom temperature of 92° C. The column top fraction obtained from the distillation column B (crude purification step), which contains HF and 2-chloro-3,3,3-trifluoropropene as main components, was supplied to the reactor 2 in the next tetrafluoropropene-producing procedure, and the column bottom fraction, which contains HF as a main component, was recycled to the reactor 1.

A Hastelloy reactor with a capacity of 7.8 L was used as a reactor for the tetrafluoropropene-producing procedure (reactor 2), and 6.5 kg of chromium oxide containing $CrO_2$ as a main component was placed in the reactor as a catalyst. The operating conditions in the distillation column C were as follows: a pressure of 0.75 MPa, a column top temperature of 3.7° C., and a column bottom temperature of 92° C.

Fluorination treatment of the catalyst before the reaction in the reactor 1 (trifluoropropene-producing step) and the catalyst before the reaction in the reactor 2 (tetrafluoropropene-producing procedure) and heating of the reactors were performed in the same manner as in Example 1. Thereafter, an operation of the process started under the operating conditions shown in Table 11. The composition of components in each step of the reaction process was analyzed using gas chromatography in the same manner as in Example 1. Table 12 shows the results.

TABLE 11

| Reaction Step | Reaction Temperature (° C.) | Pressure (MPa) |
| --- | --- | --- |
| Reactor 1 | 300 | 0.1 |
| Reactor 2 | 365 | 0.1 |

| Distillation Step | Column Top Temperature (° C.) | Column Bottom Temperature (° C.) | Pressure (MPa) |
| --- | --- | --- | --- |
| Distillation Column A | −31 | 91 | 0.75 |
| Distillation Column B | 65 | 92 | 0.75 |
| Distillation Column C | 3.7 | 92 | 0.75 |

TABLE 12

| | $O_2$ (kmol/hr) | HCl (kmol/hr) | HF (kmol/hr) | 1234yf (kmol/hr) | 245cb (kmol/hr) | 1233xf (kmol/hr) | 240db (kmol/hr) |
| --- | --- | --- | --- | --- | --- | --- | --- |
| ① | 0.00 | 0.00 | 5.10 | 0.00 | 0.00 | 0.00 | 1.50 |
| ② | 0.00 | 0.00 | 30.0 | 0.00 | 0.00 | 0.01 | 1.50 |
| ③ | 0.00 | 6.00 | 25.5 | 0.00 | 0.00 | 1.51 | 0.00 |
| ④ | 0.00 | 5.94 | 0.00 | 0.00 | 0.00 | 0.00 | 0.00 |
| ⑤ | 0.00 | 0.06 | 25.5 | 0.00 | 0.00 | 1.51 | 0.00 |
| ⑥ | 0.00 | 0.06 | 0.60 | 0.00 | 0.00 | 1.49 | 0.00 |
| ⑦ | 0.00 | 0.00 | 24.9 | 0.00 | 0.00 | 0.01 | 0.00 |
| ⑧ | 1.02 | 0.00 | 1.00 | 0.00 | 0.00 | 0.00 | 0.00 |
| ⑨ | 1.02 | 0.06 | 93.6 | 0.01 | 0.30 | 9.34 | 0.00 |
| ⑩ | 1.02 | 1.54 | 92.0 | 1.50 | 0.30 | 7.85 | 0.00 |
| ⑪ | 1.02 | 1.54 | 0.00 | 1.49 | 0.00 | 0.00 | 0.00 |
| ⑫ | 0.00 | 0.00 | 92.0 | 0.01 | 0.30 | 7.85 | 0.00 |

As is clear from Tables 11 and 12, 2,3,3,3-tetrafluoropropene can be continuously obtained in the process shown in FIG. 1; however, since a distillation column for separating HCl is disposed for each of the trifluoropropene-producing step and the tetrafluoropropene-producing procedure, cooling must be performed for each distillation step. It is thus necessary to repeat heating and cooling during each reaction step and each distillation step respectively, and it is clear that this process increases energy costs and equipment costs.

The invention claimed is:

1. A method for producing 2-chloro-1,1,1,2-tetrafluoropropane, comprising the reaction steps of:
   (1) obtaining 2-chloro-3,3,3-trifluoropropene by reacting a fluorinating agent with at least one chlorine-containing compound selected from the group consisting of 1,1,1,2,3-pentachloropropane, 2,3-dichloro-1,1,1-trifluoropropane, and 1,1,2,3-tetrachloropropene; and (2) obtaining 2-chloro-1,1,1,2-tetrafluoropropane by adding hydrogen fluoride to the 2-chloro-3,3,3-trifluoropropene, wherein the reaction is carried out in gas phase, wherein reaction step (1) is performed in a first reactor and reaction step (2) is performed in a second reactor, wherein the first reactor and the second reactor each comprise an outlet, the method further comprising the step of supplying the products obtained from the outlet of the first reactor and the products obtained from the outlet of the second reactor to a single distillation apparatus to separate the products into a hydrogen chloride-containing fraction and a fraction free of hydrogen chloride which comprises 2-chloro-1,1,1,2-tetrafluoropropane as a major component, wherein the products obtained from the outlet of the first reactor and the products obtained from the outlet of the second reactor are mixed prior to being supplied to the single distillation apparatus.

2. The method for producing 2-chloro-1,1,1,2-tetrafluoropropane according to claim 1, wherein reaction step (1) is performed by reacting anhydrous hydrogen fluoride with at least one chlorine-containing compound selected from the group consisting of 1,1,1,2,3-pentachloropropane, 2,3-dichloro-1,1,1-trifluoropropane, and 1,1,2,3-tetrachloropropene in a gas phase in the presence of a fluorination catalyst while heating.

3. The method for producing 2-chloro-1,1,1,2-tetrafluoropropane according to claim 1, further comprising the step of removing hydrogen chloride from the hydrogen chloride-containing fraction.

4. The method for producing 2-chloro-1,1,1,2-tetrafluoropropane according to claim 3, further comprising the step of recycling all or part of the fraction from which hydrogen chloride has been removed to at least one of the reaction steps.

5. The method for producing 2-chloro-1,1,1,2-tetrafluoropropane according to claim 1, further comprising the step of collecting 2-chloro-1,1,1,2-tetrafluoropropane from the hydrogen chloride-containing fraction and/or the fraction free of hydrogen chloride.

6. The method for producing 2-chloro-1,1,1,2-tetrafluoropropane according to claim 1, further comprising the step of recycling all or part of the fraction free of hydrogen chloride to at least one of the reaction steps.

* * * * *